(12) United States Patent
Retz

(10) Patent No.: US 8,418,534 B2
(45) Date of Patent: Apr. 16, 2013

(54) METHODS AND APPARATUS FOR DETECTION OF AIR INGRESS INTO CRYOGEN VESSELS

(75) Inventor: Patrick William Retz, Witney (GB)

(73) Assignee: Siemens Plc., Frimley, Camberley (GB)

( * ) Notice: Subject to any disclaimer, the term of this patent is extended or adjusted under 35 U.S.C. 154(b) by 313 days.

(21) Appl. No.: 12/702,484

(22) Filed: Feb. 9, 2010

(65) Prior Publication Data

US 2010/0199765 A1 Aug. 12, 2010

(30) Foreign Application Priority Data

Feb. 10, 2009 (GB) .................................. 0902155.1

(51) Int. Cl.
*G01N 15/06* (2006.01)

(52) U.S. Cl.
USPC ............................. 73/61.75; 73/579; 62/51.1

(58) Field of Classification Search .......................... None
See application file for complete search history.

(56) References Cited

U.S. PATENT DOCUMENTS

| | | | |
|---|---|---|---|
| 3,317,074 A * | 5/1967 | Long et al. ................ | 220/560.15 |
| 5,136,885 A | 8/1992 | Liebermann et al. | |
| 5,522,232 A * | 6/1996 | Nojiri ............................. | 62/140 |
| 6,156,578 A | 12/2000 | Tom | |

FOREIGN PATENT DOCUMENTS

| | | |
|---|---|---|
| DE | 3641842 A1 | 6/1988 |
| WO | WO 98/32006 | 7/1998 |

OTHER PUBLICATIONS

Specification Sheet of Telonic Instruments Limited for Quartz Crystal Microbalances and Cryogenic QCMs (2009).

"The Study of Spacecraft Surface Environment Contamination and Calibration of the Quartz Crystal Microbalance," Chinese University Thesis dated May 25, 2007.

* cited by examiner

*Primary Examiner* — Hezron E Williams
*Assistant Examiner* — Mark A Shabman
(74) *Attorney, Agent, or Firm* — Schiff Hardin LLP

(57) ABSTRACT

In an apparatus and a method for detecting deposition of solid frost caused by air ingress into a cryogen vessel, a quartz crystal microbalance, that includes a crystal sensor, is placed within the cryogen vessel, and an actuating circuit actuates resonance of the crystal sensor, and detection equipment detects a change in the resonant characteristics of the crystal sensor caused by frost deposition on the crystal sensor, and signaling equipment indicates the detected change.

11 Claims, 2 Drawing Sheets

METHODS AND APPARATUS FOR DETECTION OF AIR INGRESS INTO CRYOGEN VESSELS

BACKGROUND OF THE INVENTION

1. Field of the Invention

The present invention relates to methods and apparatus for detection of air ingress into cryogen vessels. It is particularly related to the detection of air ingress into cryogen vessels used to cool superconducting magnets used in imaging systems such as magnetic resonance imaging, nuclear magnetic resonance imaging and nuclear magnetic spectroscopy. The invention, however, may be applied to the detection of air ingress into any cryogen vessel.

2. Description of the Prior Art

FIG. 1 shows a conventional arrangement of a cryostat including a cryogen vessel that, when seen in the sectional view of FIG. 1 has an outer wall 12 and an inner wall 12a. A cooled superconducting magnet 10 is provided within the cryogen vessel, itself retained within an outer vacuum chamber (OVC) that, when seen in the sectional view of FIG. 1, has an outer wall 14 and an inner wall 14a. One or more thermal radiation shields 16 and 16a are provided in the vacuum space between the cryogen vessel and the outer vacuum chamber. In some known arrangements, a refrigerator 17 is mounted in a refrigerator sock 15 located in a turret 18 provided for the purpose, toward the side of the cryostat. Alternatively, a refrigerator 17 may be located within access turret 19, which retains access neck (vent tube) 20 mounted at the top of the cryostat. The refrigerator 17 provides active refrigeration to cool cryogen gas within the cryogen vessel, in some arrangements by re-condensing it into a liquid. The refrigerator 17 may also serve to cool the radiation shields 16 and/or 16a. As illustrated in FIG. 1, the refrigerator 17 may be a two-stage refrigerator. A first cooling stage is thermally linked to the radiation shields 16 and 16a, and provides cooling to a first temperature, typically in the region of 80-100K. A second cooling stage provides cooling of the cryogen gas to a much lower temperature, typically in the region of 4-10K.

A negative electrical connection 21a is usually provided to the magnet 10 through the body of the cryostat. A positive electrical connection 21 is usually provided by a conductor passing through the vent tube 20.

For fixed current lead designs, a separate vent path (auxiliary vent) (not shown in FIG. 1) may be provided as a fail-safe vent in case of blockage of the vent tube 20.

The cryogen 22 is typically liquid helium at a temperature of about 4K, although other cryogens may be used such as liquid hydrogen, liquid neon or liquid nitrogen. At service intervals, it is necessary to remove the refrigerator 17, and to open the vent tube 20. There is a risk that air could enter the cryogen vessel when the refrigerator is removed, or when the vent tube 20 is opened.

If air enters the cryogen vessel, it will be frozen as a frost, near its ingress point. With higher-temperature cryogens, such as nitrogen, only the water contained in air may be frozen. In any case, a frost will be deposited around the air ingress point. This may block the access for the refrigerator, which will degrade the performance of the refrigerator, leading to a rise on temperature and pressure within the cryogen vessel, in turn leading to increased consumption of cryogen. The frost deposit may build up around the vent tube 20. The vent tube serves to allow boiled-off cryogen gas to escape from the cryogen vessel, and is particularly important in the case of a magnet quench. During a magnet quench, a superconductive magnet suddenly becomes resistive, and loses all of its stored energy to the cryogen. This results in very rapid boil-off of cryogen. If the vent tube is constricted, or even blocked, then dangerously high pressure may build up within the cryogen vessel.

Removal of a frost deposit from the inside of the cryogen vessel requires removing all of the cryogen and allowing the cryogen vessel and the magnet or other equipment within it to warm up—for example, to room temperature. This is a time consuming and costly process, as the removed cryogen will need to be replenished, and, in the case of a superconducting magnet, a shimming operation may need to be performed to correct any changes in magnetic field homogeneity which may have been brought about by the warming and re-cooling of the magnet. During this whole process, the apparatus cooled within the cryogen vessel, and the system of which it forms a part, is unusable. This may have consequential effects such as patients being unable to be imaged, and maladies remaining undiagnosed. It is therefore not practical to warm the cryogen vessels and their contents as a preventative service operation. However, by not performing such preventative measures, the danger of blockages and excessive cryogen pressures remains.

SUMMARY OF THE INVENTION

The present invention is to provide apparatus and methods for detecting the presence of frost inside the cryogen vessel. The presence of a frost may then be signaled to a user or a service technician, and the warming of the cryogen vessel may be planned, for a convenient time, in order to remove the frost.

The above object is achieved in accordance with the present invention by an apparatus and a method for detecting deposition of solid frost caused by air ingress into a cryogen vessel, wherein a quartz crystal microbalance, that includes a crystal sensor, is placed within the cryogen vessel, and an actuating circuit actuates resonance of the crystal sensor, and detection equipment detects a change in the resonant characteristics of the crystal sensor caused by frost deposition on the crystal sensor, and signaling equipment indicates the detected change.

DESCRIPTION OF THE PREFERRED EMBODIMENTS

The present invention employs a Quartz Crystal Microbalance (QCM) to detect the deposition of frost, and to indicate this to a user or service technician.

A QCM includes a crystal sensor composed of a slice of AT-cut quartz crystal, with electrodes positioned on its opposing faces. In operation, it uses the reverse piezoelectric effect—that when a voltage is applied across the electrodes, some deformation of the crystal will result. A tuned resonant electrical circuit is applied to the electrodes, across the quartz crystal. The resonant circuit is tuned to the resonant frequency of the quartz crystal, typically in the range 10-20 MHz, and the resonance of the quartz crystal is indicated by a minimum of current flowing in the tuned circuit when it operates at the resonant frequency of the crystal sensor.

The quality of resonance, measured by the Q-factor, is an indication of the sharpness of the resonance with varying frequency. The Q-factor characterizes the resonance by the ratio of its bandwidth to the resonant frequency. An alternative measure is the dissipation D, which is the inverse of the Q-factor.

Figure 1:
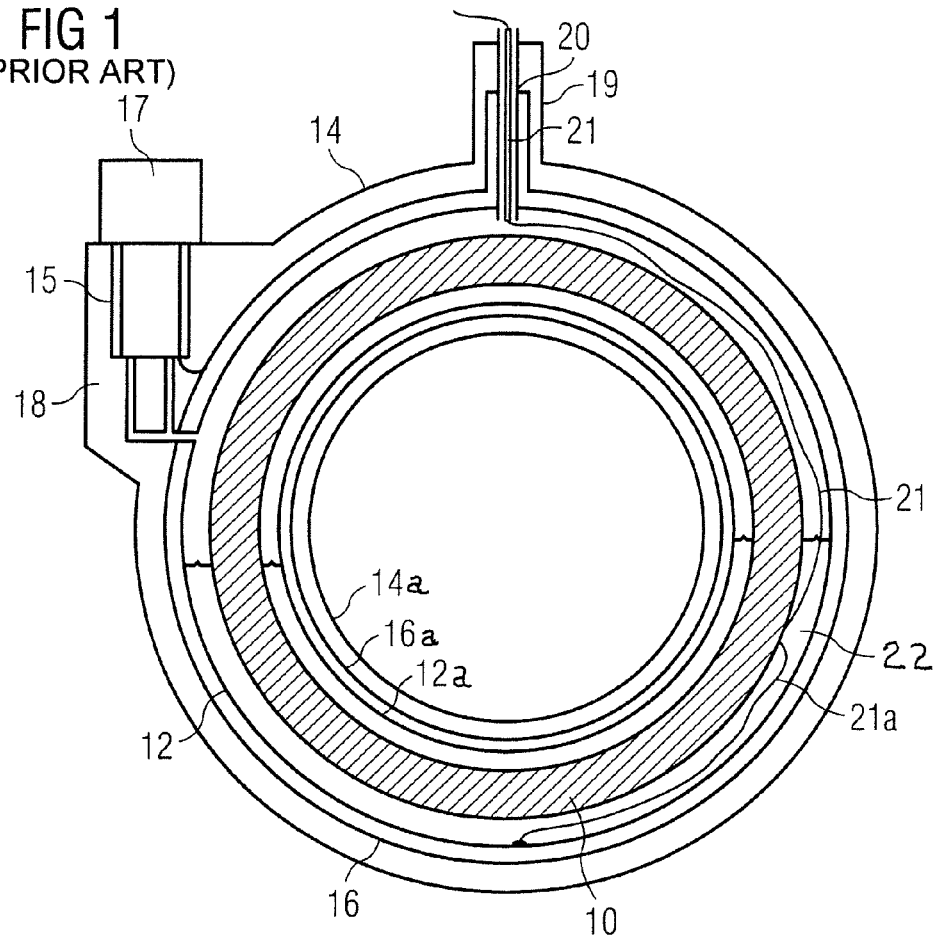
FIG. 1 shows a conventional arrangement of a cryostat including a cryogen vessel.
Figure 2A:
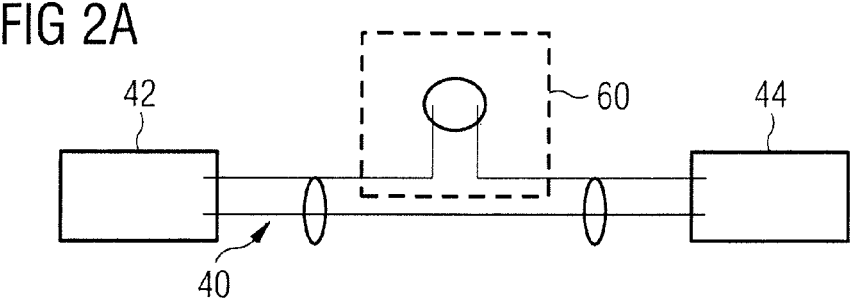
FIGS. 2A and 2B illustrate and example circuit which may be used to measure the resonant frequency, and Q-factor of resonance, of a QCM crystal.
Figure 2B:
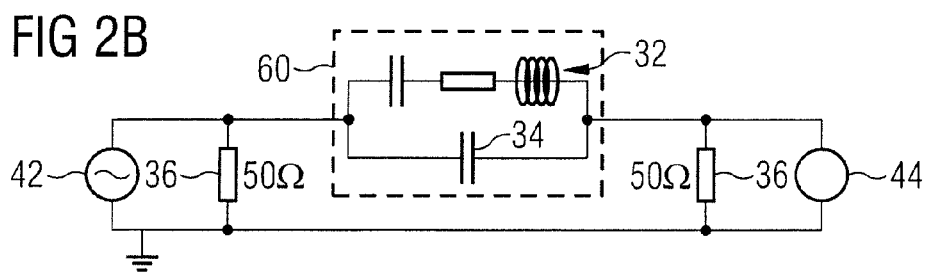

FIGS. 2A and 2B illustrate an example circuit which may be used to measure the resonant frequency, and Q-factor of resonance, of a QCM crystal.

As illustrated in FIG. 2A, the QCM crystal 60 is electrically connected into the signal line of a 50Ω coaxial cable 40. One end of the coaxial cable is connected to a frequency synthesizer 42, while the other end is connected to measuring apparatus 44, for example a digital voltmeter (DVM).

FIG. 2B shows an approximate electrical schematic diagram. The QCM crystal 60 is represented by its approximate equivalent circuit: a series combination 32 of capacitor, resistor and inductor in parallel with a capacitor 34. The labeled 50Ω impedances 36 represent the characteristic impedance of the coaxial cable 40. As viewed from the frequency synthesizer, the QCM crystal and the 50Ω impedance 36 of the coaxial cable in front of the DVM form a potential divider. To test the resonance frequency, and the Q-factor of resonance, of the QCM crystal 60, the output of the frequency synthesizer 42 is made to sweep through a range of frequencies, which includes the expected resonant frequency. As the frequency output by the frequency synthesizer 42 reaches the series resonant frequency of the QCM crystal, the impedance of the series branch 32 falls to a minimum. By consequence, the output to the DVM becomes a maximum. This maximum can be detected, and the frequency at which it occurs can be used to determine the series resonant frequency. As the frequency generated by the frequency synthesizer 42 is further increased, a parallel resonance condition occurs in which the combination of series branch 32 and parallel capacitance 34 resonate. At that frequency, a maximum impedance of the QCM crystal 60 occurs, indicated by a minimum DVM signal.

This arrangement may be used to initially determine the resonant frequency and the Q factor of the QCM crystal, and may also be used for measurements of the crystal in use.

In embodiments of the present invention, the crystal sensor 60 is placed inside the cryogen vessel in regions where the formation of ice would be undesirable. The frequency synthesizer, and other apparatus, may be placed outside of the cryogen vessel, electrically connected to the crystal sensor.

When material, such as a frost of water, nitrogen or other contaminant, is deposited on the crystal sensor, its resonant frequency will change as a result of the increased effective mass of the crystal sensor.

Figure 3:
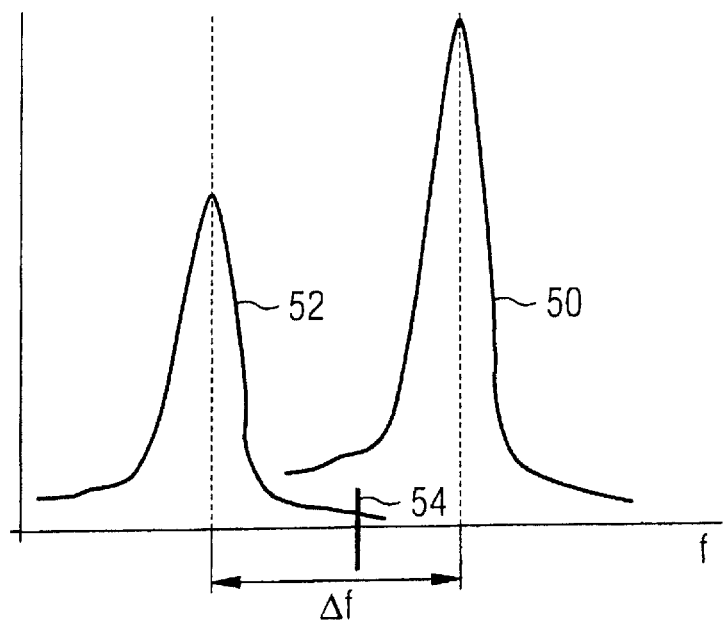
FIG. 3 shows an example in the change in resonant response of the QCM crystal sensor.

FIG. 3 shows an example in the change in resonant response of the QCM crystal sensor in response to a deposition of a frost on the crystal. The initial resonant peak 50, shown to the right of the drawing, represents the natural resonant response of the QCM crystal sensor, when it is free from any deposits on its surface. The detected resonant peak 52 represents the resonant response of the QCM crystal sensor once a deposit has occurred on the surface of the QCM crystal sensor. The added mass causes the resonant frequency to fall. In a liquid or gas, the quality (Q-factor) of the resonance would also be reduced, indicated by the lower and wider resonance peak. As will be apparent to those skilled in the art, the change in frequency and quality of the resonant response of the QCM may be detected by suitable circuitry connected to measure the voltage across, and current through, the QCM crystal. For example, the circuitry as described with reference to FIGS. 2A and 2B may be used.

Once resonance is detected at a frequency below a certain threshold, for example, the frequency indicated at 54 in FIG. 3, a solid deposit may be deemed to have occurred on the QCM crystal sensor. This fact can be indicated to a user or to a service technician by any suitable known signaling equipment—an indicator lamp, an audible warning, telephone, SMS text message, email, fax and so on. A service visit may be scheduled, to remove the cryogen from the cryogen vessel, and warm it up to room temperature. In the case of a water-based deposit, it may be preferred to warm the interior of the cryogen vessel above room temperature, to speed up the evaporation of the water.

A QCM can also be used to detect a change in gas density. This may be useful for detecting air ingress which does not form a frost on the crystal sensor. For example, in a helium-filled cryogen vessel, the ingress of nitrogen will produce a noticeable change in the density of the gas. This may also be detected by the QCM as a change in the Q-factor of the resonant response.

Where the QCM is used to measure the change in the composition of the gas within the cryogen vessel, for example, to detect the appearance of nitrogen mixed into a helium environment, the mass of the QCM crystal will not change. The viscosity encountered by the crystal will change, from the viscosity of a helium environment to the viscosity of an environment composed of a mixture of helium and nitrogen. Similarly, the density of the gaseous environment will change from that of a helium environment to that of an environment composed of a helium and nitrogen mixture. This change will cause the frequency and quality (Q-factor) of the resonance characteristic to reduce. This may be detected by a suitable detection circuit, for example by comparing the resonant frequency and/or the Q-factor to a respective predetermined threshold 54. The detection may be used to alert a user or a service technician to the detected ingress of air.

With the QCM crystal placed near the source of air ingress, the gas density experienced by the QCM crystal will change if air enters the cryogen vessel. This will cause the QCM crystal's resonant frequency and Q-factor to be modified. These effects may be relied upon to detect the air ingress. In cryogen vessels cooled to below the freezing point of nitrogen, the QCM crystal may be placed further inside the cryogen vessel, where deposition of solid nitrogen frost may be expected. A solid nitrogen frost may be detected and removed as discussed above.

Figure 4:
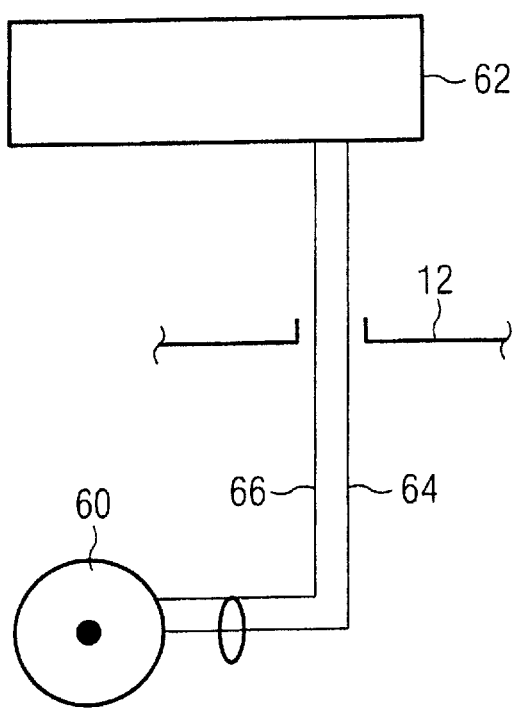
FIG. 4 schematically illustrates an example arrangement of a QCM crystal within a cryogen vessel.

FIG. 4 schematically illustrates an example arrangement of the QCM crystal 60 within the cryogen vessel 12, while frequency synthesizer 62 lies outside of the cryogen vessel, typically at room temperature. The frequency synthesizer 62 may produce an oscillating current at a frequency of about 20 MHz.

The provision of the QCM crystal sensor 60 inside the cryogen vessel 12 will require the provision of at least one further electrical connection 64 into the cryogen vessel—the second electrical connection 66 may be made through the earth connection of the body of the cryogen vessel, assuming that it is made of a metal. Preferably, however, both electrical connections are made by wires leading into the cryogen vessel, to remove any possible effects of the resistance of the cryogen vessel on the resonant response. Preferably, this is achieved by use of a coaxial cable 40 as discussed with reference to FIG. 2A.

In an alternative arrangement, an oscillator circuit is provided inside the turret of the cryogen vessel. This applies the initial resonant frequency to the QCM crystal. Connections are provided to outside the cryogen vessel, enabling the direct measurement of the frequency and the measurement of the magnitude of the signal at resonance. This allows simple calculation of the Q-factor. The power source may be mounted outside the cryostat.

The QCM crystal sensor 60 and its associated wiring 64, 66 may be placed in the appropriate position within the cryogen vessel 12 during manufacture of the cryogen vessel. Alternatively, the QCM crystal sensor 60 may be retrofitted to a cryogen vessel 12 during a service. For example, the wires 64, 66 may be passed through a siphon port, conventionally provided to the cryogen vessel, allowing fitting without disturbing any other connections.

The QCM crystal sensor is driven at its resonant frequency and consumes very little power. This is important as any power consumed by the QCM crystal sensor is dissipated as heat within the cryogen vessel, leading to loss of cryogen or additional load onto the refrigerator.

A QCM suitable for use at temperatures below 10K is available from TELONIC INSTRUMENTS LIMITED, Wokingham RG41 1QN UK (www.telonic.co.uk) under reference M16-17-18.

The natural resonant frequency 50 of the QCM crystal is determined by the material and thickness of the crystal. It may be best to determine the natural resonant frequency by observation. Determination of the resonant frequency of the crystal sensor may be performed by wither of the following methods, or by the method described with reference to FIGS. 2A and 2B.

Using the circuit of FIG. 2B, the frequency synthesizer may apply an AC voltage of a frequency corresponding to the approximate expected resonant frequency of the crystal sensor. The resonant frequency is determined from monitoring the voltage detected by DVM 44, and varying the frequency of the applied AC voltage until a maximum value of voltage is detected by the DVM 44. Intermittently, or constantly, the applied AC voltage may be varied slightly in frequency, to ensure that its frequency matches the resonant frequency of the crystal sensor. A data output from the AC voltage generator may be employed to indicate the resonant frequency of the crystal sensor.

Alternatively, at intervals or continuously, an AC voltage of varying frequency is applied to the crystal sensor, and the corresponding voltages detected by DVM 44. Once the voltages have been recorded over a range of applied AC frequencies, the highest voltages detected by DVM 44 may be determined, and this will indicate the resonant frequency of the crystal sensor at the time. An advantage of this method is that the Q-factor at the time may be determined by consideration of the rate and magnitude of the change in voltages detected by DVM 44 at frequencies close to the resonant frequency, both greater and less than the resonant frequency itself, The methods described in the preceding two paragraphs may also be used for detecting variation in the resonant frequency of the QCM crystal, during operation in detecting air ingress.

Although modifications and changes may be suggested by those skilled in the art, it is the intention of the inventor to embody within the patent warranted hereon all changes and modifications as reasonably and properly come within the scope of his contribution to the art.

I claim as my invention:

1. A cryostat comprising:
    a cryogen vessel;
    a quartz crystal microbalance comprising a quartz sensor placed within said cryogen vessel, and an actuating circuit that actuates resonance of the crystal sensor;
    detection equipment that detects a change in resonant characteristics of said quartz sensor caused by deposition of solid frost on said crystal sensor; and
    signaling equipment that indicates the detected change.

2. Apparatus according to claim 1 wherein the detection equipment is configured to detect a resonant frequency of the crystal sensor falling below a threshold value.

3. Apparatus according to claim 1 wherein the detection equipment is configured to detect a Q-factor of the resonance of the crystal sensor falling below a threshold value.

4. Apparatus according to claim 1 wherein the crystal sensor is located within the cryogen vessel and the detection equipment is located outside of the cryogen vessel, the crystal sensor being electrically connected to the detection equipment.

5. A cryostat as claimed in claim 1 wherein said cryogen vessel comprises a location at which air ingress into said cryogen vessel is expected to occur, and wherein said crystal sensor is placed within said cryogen vessel at said location at which said air ingress occurs.

6. A method for detecting deposition of a solid frost of nitrogen caused by air ingress into a cryogen vessel, comprising:
    providing a quartz crystal microbalance, comprising a crystal sensor placed within the cryogen vessel;
    detecting a change in resonant characteristics of the crystal sensor caused by deposition of said frost on the crystal sensor; and
    indicating the detected change.

7. A method according to claim 6 comprising detecting said change by detecting a resonant frequency of the crystal sensor falling below a threshold value.

8. A method according to claim 6 comprising detecting said change by detecting a Q-factor of the resonance of the crystal sensor falling below a threshold value.

9. A method as claimed in claim 6 wherein said cryogen vessel has a structural location at which said air ingress is expected to occur, and comprising placing said quartz crystal microbalance within said cryogen vessel near said location at which said air ingress is expected to occur.

10. A cryostat comprising:
    a cryogen vessel;
    a quartz crystal microbalance comprising a quartz sensor faced within said cryogen vessel, and an actuating circuit that actuates resonance of the quartz sensor;
    detection equipment that detects a change in resonant characteristics of said quartz sensor caused by a change in at least one of density and viscosity of gas in said cryogen vessel; and
    signaling equipment that indicates the detected change.

11. A cryostat as claimed in claim 10 wherein said cryogen vessel comprises a location at which air ingress into said cryogen vessel is expected to occur, and wherein said quartz sensor is placed within said cryogen vessel at said location at which said air ingress is expected to occur.

* * * * *